United States Patent [19]

Gibson

[11] 3,998,884

[45] Dec. 21, 1976

[54] CATALYTIC CONVERSION OF PHENOL TO CYCLOHEXANOL AND/OR CYCLOHEXANONE

[75] Inventor: Charles Arnold Gibson, South Charleston, W. Va.

[73] Assignee: Union Carbide Corporation, New York, N.Y.

[22] Filed: Apr. 4, 1975

[21] Appl. No.: 565,086

[52] U.S. Cl. .................. 260/586 P; 260/631 H
[51] Int. Cl.² ............... C07C 27/00; C07C 29/20; C07C 45/00
[58] Field of Search ................ 260/631 H, 586 P

[56] References Cited

UNITED STATES PATENTS

| | | | |
|---|---|---|---|
| 2,087,691 | 7/1937 | Lazier | 260/586 P |
| 2,328,719 | 9/1943 | Houghton et al. | 260/586 P |
| 2,574,078 | 11/1951 | Whitaker et al. | 260/586 P |
| 2,829,166 | 4/1958 | Joris et al. | 260/586 P |
| 2,857,432 | 10/1958 | Joris | 260/586 P |
| 2,873,296 | 2/1959 | Nillsson et al. | 260/586 P |
| 3,076,810 | 2/1963 | Duggan et al. | 260/586 P |
| 3,305,586 | 2/1967 | Phielix | 260/586 P |

OTHER PUBLICATIONS

Adkins, "Reactions of Hydrogen" pp. 56–62 (1937).
Mallinckrodt, "Lab. Chemicals," (1960) pp. 171–172.

*Primary Examiner*—Norman Morganstern
*Attorney, Agent, or Firm*—Charles J. Metz

[57] ABSTRACT

Phenol is reacted with hydrogen in contact with a nickel catalyst, wherein the concentration of hydrogen is controlled, and/or wherein controlled amounts of water are included in the reaction mixture, to produce cyclohexanol, or preferably cyclohexanol plus cyclohexanone. Optionally, the product stream from this reaction is used as the feed stream for a dehydrogenation reaction to produce cyclohexanone.

8 Claims, 1 Drawing Figure

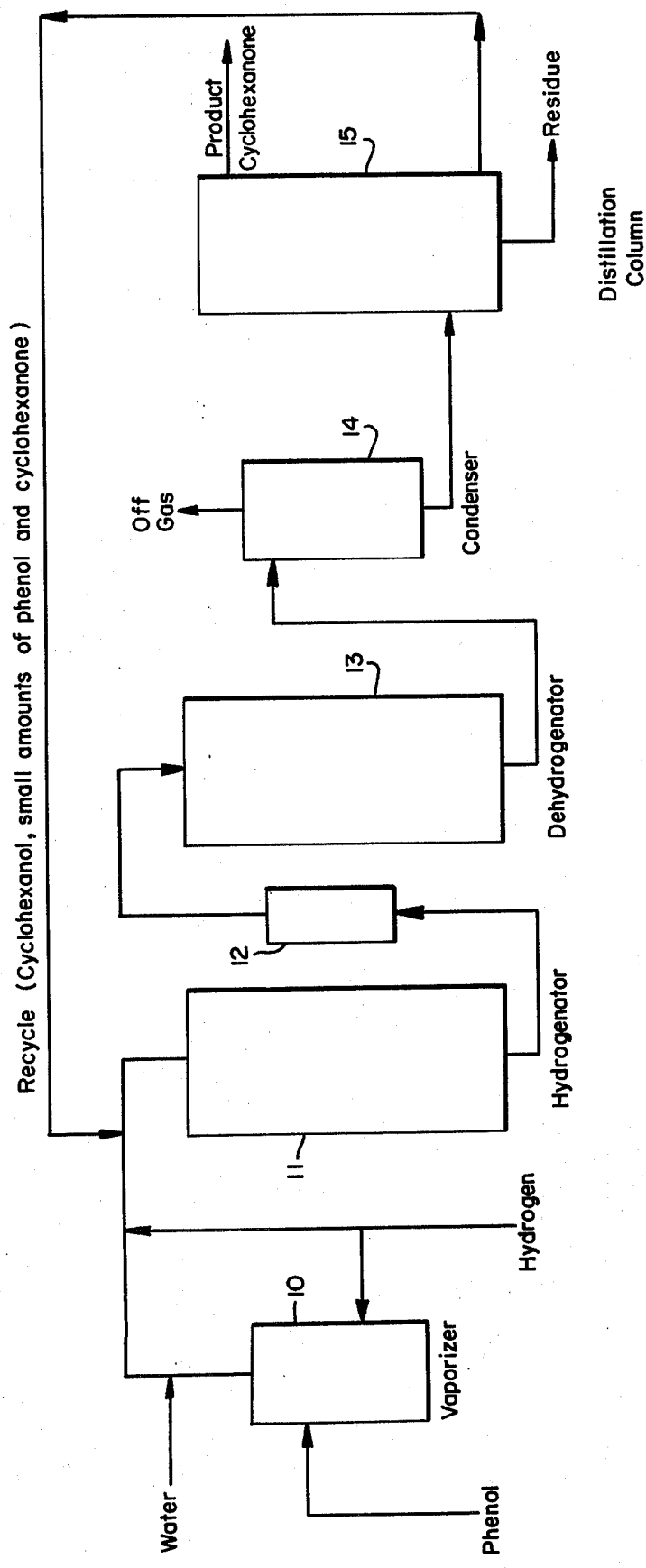

CATALYTIC CONVERSION OF PHENOL TO CYCLOHEXANOL AND/OR CYCLOHEXANONE

The invention relates to an improvement in the nickel-catalyzed hydrogenation of phenol to cyclohexanol and/or cyclohexanone.

The vapor phase hydrogenation of phenol to cyclohexanol over a nickel catalyst is known. For instance, see pages 135 and 166–167, Sabatier, "Catalysis In Organic Chemistry," translated by E. E. Reid, D. Van-Nostrand Co., New York (1922). Further, the dehydrogenation of secondary alcohols such as cyclohexanol to the corresponding ketone, over a zinc oxide catalyst, is also known. See, for instance, U.S. Pat. No. 2,179,488 (1939). These two reactions are carried out on a large commercial scale today in the production of cyclohexanone from phenol. Cyclohexanone is a valuable reactant that is used to make caprolactone, caprolactam, and other commercially valuable materials.

The present invention is based principally upon two discoveries. First, it has been found that unexpected advantages are obtained by employing diluted hydrogen containing a controlled proportion of hydrogen, as the reducing gas in the vapor phase, nickel catalyzed, hydrogenation of phenol to cyclohexanol. And second, it has been found that the inclusion of controlled amounts of water in the reaction mixture, also yields unexpected advantages in the nickel catalyzed, vapor phase hydrogenation of phenol to cyclohexanol.

In a first major aspect, the invention provides a process wherein a vapor phase reaction mixture comprising (a) phenol, and (b) a gas containing from about 30 to about 65 mole per cent hydrogen, the remainder of said gas being composed principally of inert gases, is contacted with a metallic nickel hydrogenation catalyst at an elevated temperature sufficient to produce cyclohexanol, or, preferably, cyclohexanol plus cyclohexanone.

In a second major aspect, the invention provides a process wherein a vapor phase reaction mixture comprising phenol, hydrogen, and controlled amounts of water, are contacted with a metallic nickel hydrogenation catalyst at an elevated temperature sufficient to produce cyclohexanol, or, preferably, cyclohexanol plus cyclohexanone. Additional aspect of the invention include both the use of diluted hydrogen and at the same time, the use of controlled amounts of water in the hydrogenation process, as well as a series reaction wherein the product stream from the hydrogenation is employed, without intermediate condensation, as the feed stream in a subsequent zinc oxides-catalyzed dehydrogenation, to produce cyclohexanone.

The single FIGURE is a schematic flow diagram of a process embodying the principles of the invention.

Referring to the drawing, phenol is fed to a vaporizer 10, into which a portion of the hydrogen stream is also fed. The vaporized phenol and hydrogen mixture flows from this vaporizer 10 to the top of a tubular reactor 11. Water, the remainder of the hydrogen stream, and a recycle stream, are also fed to the line connecting the vaporizer 10 with the tubular reactor 11. The reactor 11 contains metallic nickel catalyst. Said reactor 11 is provided with cooling means, because the hydrogenation reaction is exothermic.

The product stream from the hydrogenation reactor 11, which contains cyclohexanol, cyclohexanone, some unreacted phenol, and unreacted gas from the hydrogen stream, is fed through a heat exchanger 12 to another tubular reactor 13, in which a dehydrogenation reaction is catalyzed by a zinc oxide catalyst. The product stream from the dehydrogenation reactor 11 contains cyclohexanone, unreacted gas from the hydrogen stream, small amounts of phenol and cyclohexanol, and by-products. Said product stream flows from the reactor 13 to a condenser 14. The unreacted gas from the hydrogen stream is separated in the condenser 14, and the remaining materials are condensed. The condensate from the condenser 14 is introduced into a distillation column 15, from which cyclohexanone is taken off as an overhead product, a recycle stream containing cyclohexanol with small amounts of cyclohexanone and phenol is removed, and a residue product is removed from the bottom.

In accordance with the first major aspect of the invention, the hydrogen feed stream contains from about 30 to about 65 and preferably from about 45 to about 55, mole per cent hydrogen, the remainder being composed principally of inert gases such as methane, nitrogen, or the like. The preferred inert gas is methane. When proportions of hydrogen lower than those indicated are employed, the dew point of the feed and reactant streams becomes lower, and so the feed streams must be heated to a higher temperature in order to avoid condensation of phenol. Also, when a second reaction stage is employed (i.e., a dehydrogenation to produce cyclohexanone), it is desired to have a small proportion of hydrogen in the feed to the dehydrogenator in order to achieve maximum efficiency. Therefore, proportions of hydrogen in the feed stream below those indicated, tend to yield too low a concentration of hydrogen in the feed to the second stage to achieve the maximum efficiency mentioned above. When the concentration of hydrogen in the feed is greater than indicated, there tends to be essentially complete conversion to the alcohol, instead of producing significant quantities of the ketone, which is the desired ultimate product. Also, with higher concentration of hydrogen, the blow off gas will contain large proportions of hydrogen, and will therefore be uneconomical to burn.

When water is introduced into the feed in accordance with the second major aspect of the invention, the proportions employed are usually from about 0.5 to about 3 weight per cent, based on weight of phenol. With amounts less than about 0.5 weight per cent, the beneficial effects (which are described below in the Examples) tend to diminish. No additional benefit is obtained by using more than 3 per cent. Preferred proportions of water are from about 1 to about 2 weight per cent.

In both major aspects of the invention, hydrogen is employed in an amount sufficient to hydrogenate substantially all of the phenol. Molar ratios of at least about 2.5 moles, up to about 3.5 moles, of hydrogen, per mole of phenol have been found to be acceptable for this purpose.

The catalyst employed is metallic nickel, which is normally employed as a deposit upon an inert support such as alumina.

The temperature of the hydrogenation reaction is an elevated temperature sufficient to maintain the phenol and the hydrogenated products thereof in the vapor state. Under the preferred conditions set forth herein, the dew point of the reaction mixture is about 155° C. The preferred temperature of the catalyst bed is from about 160° C., although temperatures above and below that range can be employed under certain conditions, if desired. For instance, the reaction will proceed at temperatures as low as about 100° C., if vapor state conditions are maintained (e.g., by using lower pressure and dilute reaction mixture), and at temperatures as high as about 230° C., before incidence of side reactions begin to become unacceptable.

In a continuous, vapor-phase, catalyzed reaction of this type, it is not particularly useful to discuss reaction time, contact time with the catalyst, etc. The index of reaction time or throughput rate is usually discussed in terms of space velocity (LHSV), the units being volume of reactant per volume of catalyst per hour. The LHSV of phenol in the hydrogenation reaction will usually be on the order of from about 0.2 to about 0.6.

The pressure in the reactor will usually be from about atmospheric up to about 2½ to 3 atmospheres, with a gauge pressure of about one atmosphere being most common.

While the product from the hydrogenation reaction can be recovered by standard means (said product being cyclohexanol, usually with up to about 30 mole per cent cyclohexanone), it is preferred to operate the process as the first stage of a two-stage process, the second stage being a catalyzed dehydrogenation to produce cyclohexanone. Such a two-stage process is shown in the drawing, and was discussed above in broad terms.

The feed for the second stage is the uncondensed product stream from the first stage. This stream is first heated by conventional means (as by a heat exchanger, shown as 12 in the drawing) to a temperature within the range from about 320° to about 420° C., and preferably from about 340° to about 380° C.

The catalyst for the second stage is a conventional zinc oxide dehydrogenation catalyst.

The pressure of the reaction in the second stage will be a little lower than that indicated above for the first stage.

The space velocity (volume of gas per volume of catalyst per hour) of the reaction stream in both stages is usually within the range of from about 200 to about 1000, at the temperature and pressure conditions indicated.

The product stream from the second stage is recovered by conventional means, such as that shown in the drawing and discussed above.

In the Examples below, both laboratory scale and pilot plant scale reactors were employed. The equipment arrangements in both cases were analogous to that shown in the FIGURE, except that in some cases, the two reaction stages were carried out separately. The specific catalysts employed were the following:

Hydrogenation Catalysts

Gridler G-33 and G-87 catalysts were used in the hydrogenator during the current study. The G-33 catalyst contains approximately 32 percent of nickel on a refractory aluminum-oxide, and was used in the 3/16 × 3/16 tablet size. The G-33 was received as the oxide, oxidized state, and was reduced in the laboratory with pure hydrogen and a hydrogen-methane mixture. The G-87 catalyst is an extrudate of approximately 40 percent nickel on refractory support. During the current study, G-87 extrudates which measured one-eighth by one-fourth inch were used. Some typical physical properties of G-33 and G-87 are shown below.

|  | G-33 | G-87 (extrudates) | |
|---|---|---|---|
| Size | 3/16 × 3/16 tablets | 1/8 × 1/4 | 3/16 × 1/4 |
| Bulk Density lbs./cu. ft. avg. | 60 | 55 | 55 |
| Dead Wt. Load Crush Strength | 25 pounds avg. | 18 lbs. min. | 20 lbs. min. |

Upon spot (surface) analysis, the G-87 catalyst was found to contain the following:

| Nickel | 40 weight per cent |
|---|---|
| Alumina | 56 weight per cent |
| Calcium | 2 weight per cent |
| Silicon | 2 weight per cent |
| Sodium and others | Trace |

Dehydrogenation Catalyst

The dehydrogenation catalyst for the production of cyclohexanone is Houdry-Huls H-2004. The Huls catalyst has the following approximate compositions (by weight):

| Zinc Oxide | 79 percent |
|---|---|
| Calcium Oxide | 6.6 percent |
| Potassium Oxide | 3.3 percent |
| Aluminum Oxide | 4.5 percent |
| Chromium Sesquioxide | 1.4 percent |
| Sulfate | 2.5 percent |

The catalyst measures 6 by 7 mm and is very hard.

The hydrogen employed in the Examples was unless otherwise specified, either a BTX unit (benzene-toluene-xylene) blow-off gas, or a synthetic mixture prepared in the laboratory. Typical analyses of these two gas mixtures are as follows:

| | Hydrogen-Methane mixture | |
|---|---|---|
| Components, Mol Percent | BTX Unit Blowoff | Synthetic Mixture Prepared in Lab |
| Hydrogen | 45.0 | 45.0 |
| Methane | 52.0 | 50.9 |
| Ethylene | nil | nil |
| Ethane | 0.9 | 1.4 |
| Benzene | 0.9 | 0.3 |
| Carbon Monoxide | 60 ppm | 100 |
| Nitrogen | 1.0 | 1.7 |
| Oxygen | 60 ppm | nil |
| Water | 0.5 | nil |
| Heavies | 0.1 | nil |
| Butene-1 | 0.7 | 0.7 |

The water for use in the hydrogenation must be good steam condensate. The water cannot contain heavy metals and/or salts since either is detrimental to catalyst activity. A measure of protection is afforded by adding the water to the phenol before the vaporizer. In this manner, most of the objectionable contaminates would be removed as part of the residues.

The standard laboratory equipment set-up and procedure was as follows:

Hydrogenator

The laboratory hydrogenation reactor was made from a one-inch ID by 58-inch carbon steel tube. The tube had a 35-inch jacket which was electrically heated and insulated. A rod-supported screen was inserted 19 inches up the tube to support the catalyst. A thermowell was inserted down the tube and contacted the catalyst support. The catalyst was loaded through an opening in the tube between the upper jacket portion and the flange. In the case of G-87 catalyst, size ⅛ × ¼ inch extrudate (200 milliliters) was drop loaded to form a bed with a height of 14 inches. A pre-heater section was formed in the tube above the catalyst by adding 185 milliliters of one-quarter-inch stainless steel packing. Phenol was liquified at 40° to 45° C., and water equivalent to 1.14 percent by weight of phenol was added. The phenol was pumped to the top of a one-by-fifteen inch vaporizer and allowed to enter the center of the vaporizer and run down over stainless-steel sponge packing. The hydrogen-methane gas mixture was flowed to the bottom of the vaporizer and used to carry the phenol in vapor state to the pre-heated section of the hydrogenator. The hydrogenator can be operated at atmospheric pressure or above. Thermocouples were located in the catalyst bed at 1, 3, 6, 9, and 12 inches from the top of the catalyst; however, the thermocouples may be moved at option. The jacket of the hydrogenator was electrically heated, and it has a capacity of 1,800 milliliters. "Dowtherm" was used in the jacket during the oxidation and reduction of the nickel catalyst. Toluene was used in the jacket during the hydrogenation of phenol. The liquid level on the shell side was maintained at a higher level than the top of the catalyst on the tube side. The hydrogenator can be coupled with a dehydrogenation converter to permit back-to-back vapor operation.

Dehydrogenator

The laboratory dehydrogenator was made from a one-inch ID stainless-steel tube of approximately 60 inches in length. A 37-inch section of the tube was heated by means of two electrical circuits and was insulated with 4 inches of "Kaylo". A one-by-twelve inch vaporizer was attached to the top of the tube to permit back-to-back operation with the hydrogenator. a one-by-fifteen inch vaporizer was attached to the top of the tube to permit direct liquid feed. The tube was packed with 14.5 inches of stainless-steel sponge to provide a catalyst support. The next 14.5 inches of the dehydrogenator tube contained 200 milliliters of Houdry Huls H-2004 catalyst, and a 19.25-inch section above the catalyst was filled with 205 milliliters of ¼-by-¼-inch stainless-steel packing. Feed can be made to the dehydrogenator by either vaporizing liquid cyclohexanol in a hydrogen stream or by transporting vapor from the hydrogenator outlet. The vaporizers were normally operated at 200° C., and the pre-heater was operated at the temperature of the upper portion of the catalyst bed. The catalyst bed was operated between 350° and 400° C. The tube and attachments were operated at one and two atmospheres of pressure. Thermocouples were located at 1, 4, 7, 10, and 13 inches down into the catalyst bed.

EXAMPLE 1

The laboratory hydrogenator was run, under the conditions set forth in Table I. In Runs 1–19, G-33 catalyst was used, and in Runs 20–36, G-87 catalyst was employed. In Runs 1–3, pure hydrogen was used, and in the remainder, the above-described laboratory hydrogen/methane mixture was used. The mole ratio of hydrogen to phenol was 5:1 in all cases except in Runs 26–30. The mole ratios of hydrogen to phenol in those runs were as follows:

| | | |
|---|---|---|
| 26 | — | 4.06:1 |
| 27 | — | 3.5:1 |
| 28 | — | 3.5:1 |
| 29 | — | 3.5:1 |
| 30 | — | 4.06:1 |

Table I also displays the per cent of phenol converted, the per cent yield to cyclohexanol ("OL") plus cyclohexanon ("ONE"), the efficiency based on phenol, and the proportion of cyclohexanol to cyclohexanone in the product.

The results demonstrate that, other conditions being equal, the use of diluted hydrogen rather than pure hydrogen increases the proportion of cyclohexanone (the desired ultimate product) in the product of the hydrogenation reaction, and the addition of water to the feed significantly improves the efficiency of the process.

TABLE I

HYDROGENATION OF PHENOL TO CYCLOHEXANOL

| Run No. | Liquid Hourly Space Velocity LESV | Space Velocity | Water Wt. % Based on Phenol | Vaporizer ° C Top | Vaporizer ° C Bottom | Jacket ° C | Pre-heater ° C | Catalyst Bed, ° C Inches from Top 1 | 4 | 6 | 9 | 12 |
|---|---|---|---|---|---|---|---|---|---|---|---|---|
| 1 | 0.2 | 330.5 | — | 150 | 149 | 142 | 80 | 185 | 160 | 150 | 150 | 145 |
| 2 | 0.25 | 350.5 | — | 144 | 152 | 142 | 83 | 202 | 176 | 160 | 153 | 150 |
| 3 | 0.3 | 419.0 | — | 153 | 153 | 142 | 83 | 203 | 177 | 158 | 154 | 151 |
| 4 | 0.2 | 680 | — | 158 | 137 | 145 | 86 | 184 | 179 | 168 | 159 | 156 |
| 5 | 0.25 | 851 | — | 154 | 134 | 145 | 87 | 188 | 186 | 175 | 165 | 162 |
| 6 | 0.30 | 1020 | — | 162 | 136 | 145 | 92 | 192 | 192 | — | 175 | 167 |
| 7 | 0.25 | 272 | — | 184 | 154 | 145 | 93 | 195 | 181 | — | 160 | 156 |
| 8 | 0.19 | 330 | — | 192 | 185.5 | 148 | 193.8 | 164.2 | 147.2 | 145.9 | 145.3 | 145.4 |
| 9 | 0.19 | 680 | — | 192 | 169 | 148 | 193.1 | 168.1 | 156 | 150 | 147 | 147 |
| 10 | 0.20 | 680 | — | 202 | 175 | 165 | 201 | 183.9 | 171.3 | 166 | 165 | 165 |
| 11 | 0.20 | 680 | — | 149 | 134 | 141 | 151 | 161.7 | 149.5 | 143.6 | 141 | 140.8 |
| 12 | 0.20 | 680 | — | 154 | 140 | 165 | 153 | 185.3 | 173.6 | 167.5 | 165.2 | 165.1 |
| 13 | 0.21 | 340 | — | 157 | 146 | 165 | 151 | 189.4 | 173.3 | 166.7 | 164.9 | 164.8 |
| 14 | 0.19 | 680 | — | 149 | 136 | 160 | 152.3 | 179.8 | 167.8 | 161.3 | 157.1 | 159.0 |
| 15 | 0.19 | 340 | — | 159 | 145 | 159 | 155 | 180.2 | 166.0 | 160 | 158.5 | 158.5 |
| 16 | 0.20 | 680 | — | 155 | 143 | 160 | 152 | 183.5 | 173.1 | 164.4 | 160.5 | 159.5 |
| 17 | 0.20 | 680 | — | 151 | 131 | 154 | 153 | 179.8 | 168.7 | 159.8 | 155.7 | 154.8 |
| 18 | 0.20 | 340 | — | 180 | 158 | 154 | 154 | 183.8 | 169.4 | 159.4 | 155.4 | 154.9 |
| 19 | 0.20 | 226 | — | 136 | 162 | 154 | 155 | 181.6 | 166 | 157.3 | 154.2 | 154.2 |

TABLE I-continued

HYDROGENATION OF PHENOL TO CYCLOHEXANOL

| | | | | | | | | | | | | |
|---|---|---|---|---|---|---|---|---|---|---|---|---|
| 20 | 0.19 | 680 | — | 159 | 146 | 144 | 153 | 195.5 | 170.5 | 148.5 | 142.5 | 139 |
| 21 | 0.20 | 680 | — | 149 | 137 | 135 | 148.5 | 192 | 165 | 137 | 129 | 124 |
| 22 | 0.20 | 680 | — | 137 | 133 | 125 | 134.9 | 189 | 159 | 126 | 115 | 109 |
| 23 | 0.20 | 680 | — | 120 | 126 | 115 | 124 | 195 | 153 | 120 | 108 | 103 |
| 24 | 0.20 | 680 | — | 115 | 114 | 111 | 117.4 | 180.6 | 148 | 116 | 105 | 100 |
| 25 | 0.20 | 680 | — | 134 | 149 | 140 | 149 | 191 | 165 | 142 | 139 | 138 |
| 26 | 0.25 | 694 | — | 152 | 145 | 139 | 152 | 195.5 | 175.9 | 148 | 140 | 138 |
| 27 | 0.29 | 708 | — | 159 | 152 | 140 | 152 | 196.5 | 179.8 | 154.4 | 143.5 | 139.6 |
| 28 | 0.28 | 708 | 1.14 | 149 | 151 | 140 | 152.4 | 195.6 | 179.4 | 154.0 | 143.4 | 139.6 |
| 29 | 0.30 | 708 | 1.14 | 143 | 151 | 141 | 151 | 196.6 | 180.5 | 156.5 | 145 | 141 |
| 30 | 0.25 | 694 | 1.14 | 156 | 146 | 141 | 150 | 194.1 | 178 | 151.4 | 142 | 140 |
| 31 | 0.20 | 680 | 1.14 | 152 | 137 | 140 | 150 | 187.2 | 165.9 | 143.2 | 139.2 | 138.8 |
| 32 | 0.20 | 680 | 1.14 | 149 | 134 | 130 | 150 | 183.0 | 161.7 | 135.1 | 129.8 | 128.6 |
| 33 | 0.20 | 680 | 1.14 | 140 | 132 | 120 | 136 | 176.6 | 158.9 | 128.2 | 118.1 | 113.1 |
| 34 | 0.20 | 680 | 1.14 | 141 | 131 | 114 | 131.5 | 171.5 | 156.6 | 123 | 110.8 | 105.6 |
| 35 | 0.20 | 340 | 1.14 | 162 | 149 | 120 | 147.5 | 181.9 | 146.0 | 120.8 | 115 | 111 |
| 36 | 0.20 | 340 | 1.14 | 155 | 145 | 130 | 143 | 185.0 | 149 | 131 | 129 | 128 |

| Run No. | Reactor Pressure psig | Phenol Conversion % | Yield % to ol-one | Efficiency Based on Phenol, % | OL to ONE Ratio |
|---|---|---|---|---|---|
| 1 | 0 | 99.65 | 95.80 | 96.1 | & 32.15 |
| 2 | 0 | 99.71 | 95.85 | 96.1 | 50.80 |
| 3 | 0 | 99.71 | 96.39 | 96.67 | 42.90 |
| 4 | 0 | 97.77 | 95.50 | 97.68 | 8.33 |
| 5 | 0 | 97.04 | 95.38 | 98.29 | 6.41 |
| 6 | 0 | 94.08 | 92.52 | 98.34 | 4.69 |
| 7 | 22 | 99.40 | 97.40 | 97.99 | 19.05 |
| 8 | 0 | 94.62 | 81.24 | 85.86 | 3.86 |
| 9 | 0 | 98.91 | 96.43 | 97.49 | 13.76 |
| 10 | 0 | 99.10 | 95.62 | 96.49 | 9.6 |
| 11 | 0 | 98.65 | 96.55 | 97.87 | 14.19 |
| 12 | 0 | 98.95 | 95.25 | 96.26 | 5.98 |
| 13 | 17 | 99.90 | 93.77 | 93.86 | 9.57 |
| 14 | 0 | 99.14 | 95.81 | 96.64 | 7.50 |
| 15 | 17 | 99.43 | 94.84 | 95.38 | 13.30 |
| 16 | 0 | 98.28 | 95.81 | 97.48 | 5.83 |
| 17 | 0 | 99.23 | 96.19 | 96.94 | 8.09 |
| 18 | 15 | 99.00 | 95.56 | 96.52 | 28.1 |
| 19 | 30 | 96.77 | 96.00 | 96.22 | 28.1 |
| 20 | 0 | 100.00 | 91.99 | 91.99 | 17.9 |
| 21 | 0 | 100.00 | 94.73 | 94.73 | 28.3 |
| 22 | 0 | 100.00 | 97.23 | 97.23 | 66.9 |
| 23 | 0 | 100.00 | 97.85 | 97.85 | 62.1 |
| 24 | 0 | 100.00 | 97.70 | 97.70 | 123.0 |
| 25 | 0 | 100.00 | 93.95 | 93.95 | 16.23 |
| 26 | 0 | 99.90 | 94.70 | 94.79 | 10.86 |
| 27 | 0 | 99.37 | 95.30 | 95.90 | 6.9 |
| 28 | 0 | 99.55 | 96.20 | 96.63 | 6.13 |
| 29 | 0 | 99.73 | 96.47 | 96.73 | 7.43 |
| 30 | 0 | 99.94 | 98.55 | 98.61 | 10.08 |
| 31 | 0 | 100.00 | 98.30 | 98.30 | 18.25 |
| 32 | 0 | 100.00 | 98.72 | 98.72 | 28.50 |
| 33 | 0 | 100.00 | 99.15 | 99.15 | 59.10 |
| 34 | 0 | 100.00 | 99.26 | 99.26 | 72.30 |
| 35 | 16 | 100.00 | 99.28 | 99.28 | 122.5 |
| 36 | 16 | 100.00 | 99.03 | 99.03 | 55.6 |

EXAMPLE 2

The hydrogenator and dehydrogenator were run in series, as described above, under the conditions and with the results set forth below in Tables II and III:

TABLE II

Hydrogenator Conditions:
Catalyst - 200 mls of 3/16 inch by 3/16 inch G87
Mole Ratio of Hydrogen to Phenol - 5 to 1
Phenol Feed, mls/hr. ~ 45
Hydrogen/Methane Feed, liters/hr. (S.T.P.) = 140.6
Liquid Hourly Space Velocity (LHSV) - 0.225
Reactor Pressure - 14 psig
Space Velocity - 380

| Run No. | Water Wt. % Based on PhOH | Vaporizer °C Top | Vaporizer °C Bottom | Jacket °C. | Pre-Heater °C. | Catalyst Bed, °C. Inches From Top | | | | | Hydrogenator Spot Sample[a] Analysis (Area %) | | | | |
|---|---|---|---|---|---|---|---|---|---|---|---|---|---|---|---|
| | | | | | | 1 | 4 | 6 | 9 | 12 | Lights | ONE | OL | Ether | Phenol |
| 1 | 1.14 | 157 | 149 | 132 | 150 | 189.4 | 152.5 | 126.7 | 117.5 | 113.5 | 0.8 | 0.97 | 96.66 | 1.43 | — |
| 2 | 1.64 | 158 | 135 | 130 | 145.5 | 173 | 144 | 123 | 110 | 107 | 0.3 | 0.89 | 97.47 | 1.38 | — |
| 3 | 1.64 | 158 | 136 | 127 | 146 | 188.4 | 154 | 124 | 112 | 108 | 0.5 | 0.64 | 97.53 | 1.28 | — |
| 4 | 1.64 | 149 | 143 | 120 | 145 | 187 | 156 | 117 | 107 | 101 | 0.2 | 2.54 | 96.17 | 1.06 | — |
| 5 | 1.64 | 153 | 114 | 140 | 153 | 193.2 | 180 | 155 | 144 | 138 | 0.3 | 1.06 | 95.51 | 3.07 | — |
| 6 | 1.64 | 134 | 134 | 131 | 148 | 192 | 162 | 133 | 122 | 117 | — | — | — | — | — |

TABLE II-continued

Hydrogenator Conditions:
Catalyst - 200 mls of 3/16 inch by 3/16 inch G87
Mole Ratio of Hydrogen to Phenol - 5 to 1
Phenol Feed, mls/hr. ~ 45
Hydrogen/Methane Feed, liters/hr. (S.T.P.) = 140.6
Liquid Hourly Space Velocity (LHSV) - 0.225
Reactor Pressure - 14 psig
Space Velocity - 380

| Run No. | Water Wt. % Based on PhOH | Vaporizer °C Top | Vaporizer °C Bottom | Jacket °C. | Pre-Heater °C. | Catalyst Bed, °C. Inches From Top 1 | 4 | 6 | 9 | 12 | Hydrogenator Spot Sample[a] Analysis (Area %) Lights | ONE | OL | Ether | Phenol |
|---|---|---|---|---|---|---|---|---|---|---|---|---|---|---|---|
| 7 | 1.64 | 142 | 140 | 133 | 150 | 194 | 165 | 136 | 123 | 117 | — | — | — | — | — |

[a] ONE = Cyclohexanone
OL = Cyclohexanol
Ether = Dicyclohexyl Ether

TABLE III

Dehydrogenator Conditions:
Catalyst - 200 mls of Houdry Huls H-2004
Recycle cyclohexanol, mls/hr. - 27
Liquid Hourly Space Velocity (LHSV) - 0.388
Reactor Pressure - 10 psig
Space Velocity - 433

| Run No. | Dehydrogenation Converter °C. | Dehydrogenator Effluent Liquid Samples Area % Lights | Cyclo-hexane | Benzene | ONE | OL | Ether | Phenol | Heavies | Yield Phenol[b] to ONE % | Efficiency[b] Phenol to ONE |
|---|---|---|---|---|---|---|---|---|---|---|---|
| 1 | 380 | 0.23 | 0.66 | 0.5 | 84.6 | 6.62 | 1.51 | 0.26 | 4.0 | 87.5 | 87.7 |
| 2 | 350 | 0.1 | 0.40 | 0.2 | 70.4 | 24.8 | 1.52 | 0.08 | 2.5 | 92.75 | 92.75 |
| 3 | 350 | 0.1 | 0.40 | 0.1 | 73.13 | 21.63 | 1.41 | 0.02 | 3.2 | 92.1 | 92.1 |
| 4 | 350 | 0.12 | 0.24 | 0.1 | 68.15 | 28.2 | 0.98 | 0.24 | 1.98 | 94.5 | 94.8 |
| 5 | 350 | 0.1 | 0.53 | 0.1 | 67.76 | 28.37 | 2.1 | 0.008 | 0.97 | 94.16 | 94.16 |
| 6 | 355 | 0.1 | 0.3 | 0.1 | 70.1 | 27.53 | 1.2 | 0.05 | .61 | 96.42 | 96.42 |
| 7 | 355 | 0.14 | .4 | 0.1 | 64.2 | 33.4 | 1.57 | 0.01 | 0.13 | 97.2 | 97.2 |

[b] Corrected for recycle cyclohexanone

EXAMPLE 3

In this Example, pilot plant scale equipment was used. The reactor (for both reactions) was a fifteen-foot by 0.959 inch ID steel tube in a 3-inch diameter jacket. The reactor was insulated for 400° C. service. Thermocouples and sample points were located at 12-inch intervals starting at the top of the jacketed portion of the reactor and descending. Heat transfer fluid was circulated in the jacket by means of an electrically heated reboiler which was located at the bottom of the reactor. This arrangement created a thermo-cycle with flow of the heat exchange liquid from the bottom to the top of the jacket. Pressure could be increased on the jacket to give a maximum operating temperature of 400° C. Feed to the reactor was achieved by metering liquid to the bottom of a steam heated vaporizer and at the same time introducing gas flow to the vaporizer slightly downstream of the liquid connection. The gas mixture of hydrogen and methane, was flow-controlled through a heat exchanger prior to the vaporizer which fed the reactor. The hydrogen-methane mixture was prepared by separately flow-controlling hydrogen and methane to give the desired compositions. Effluent from the reactor was passed through two water-cooled condensers which were connected in series. A back-pressure regulator was located downstream of the second receiver. The off-gas was discharged through a metering device and vented to the atmosphere. A DP cell provided pressure drop reading across the catalyst bed. Pressure gauges on the inlet to the reactor and after the final condenser afforded a total pressure drop reading for the system.

Raw Materials

Phenol: A drum of production grade phenol was used.

Hydrogen: C.P.—grade hydrogen was obtained in cylinders.

Methane: A technical grade of methane was obtained in cylinders from Matheson Gas Products. This grade has a minimum purity of 98.0 mole percent. A typical analysis is shown below:

| Component | Mole Percent |
|---|---|
| Methane | 98.5 |
| Ethane | 0.5 |
| Nitrogen | 0.6 |
| Oxygen | 0.1 |
| Carbon dioxide | 0.1 |
| Propane | 0.1 |
| Higher Alkanes | 0.1 |

The technical grade of methane contains a maximum of 15 parts per million sulfur (4). Although sulfur at this level is detrimental to the hydrogen catalyst and could not be tolerated in commercial production, the pilot plant studies were of short duration and no significant effect on the catalyst activity was expected. No effect of the sulfur content was detectable during a total of three weeks use with nickel catalyst.

Catalyst

Hydrogenation: A total of 1,850 milliliters of three-sixteenths inch Girdler G-87 catalyst was loaded into the reactor. This afforded a catalyst bed of 13 feet, and 4 inches in length.

Dehydrogenation: The catalyst for the dehydrogenation was Houdry Huls H-2004. A total of 1,850 milliliters of the Huls catalyst was used in the reactor.

Hydrogenation Studies: The reactor was charged with 1,850 milliliters of the three-sixteenths inch G-87 catalyst and purged free of air with dry nitrogen. Dowtherm was charged to the jacket. A mixture of hydrogen, 415 liters per hour, and methane, 510 liters per hour, was fed to the reactor. This gas flow provided a space velocity of 500 which is recommended by Girdler for reduction of G-87 catalyst. The Dowtherm was heated from 30° C. over a 6 hour period. This type of operation afforded a smooth temperature rise and reduction of the nickel catalyst without hazards of an exotherm. After the temperature of the catalyst rose to 360° C., at the end of a 6 hour period, the reactor was placed under 15 psig pressure. No noticeable exotherm was experienced in going from atmospheric pressure to 15 pounds gauge. The hydrogen-methane gas feed was continued for an additional 75 minutes to improve the quality of the reduction procedure. The hydrogen-methane feed was then reduced to 10 SCFH and the Dowtherm was cooled to ambient temperature. After the Dowtherm was drained from the reactor, the jacket was flushed several times with water and then filled with water to a level sufficient to provide a liquid level above the catalyst during operation. Phenol containing 1.6 percent water was pumped from a calibrated tank to the bottom of a vaporizer where it was mixed with incoming hydrogen-methane gas, vaporized and fed over the hydrogenation catalyst. The effluent from the hydrogenator was condensed in two condensers in series. The operating conditions are summarized in Table IV.

Dehydrogenation Studies: The fifteen-foot reactor which was used for the hydrogenation studies, was used also to study the dehydrogenation of cyclohexanol. The product from the hydrogenation studies was used as feed for the dehydrogenation studies. The material of construction for the 1-inch tube in the 15-foot converter was steel. Stainless steel is the recommended material of construction for the dehydrogenator.

After the 15-foot converter had been charged with Houdry Huls H-2004 catalyst, air was fed to the converted at a rate of 30 liters per hour. The air feed was continued for six hours during which time the Dowtherm was heated to 360° C. The air feed was discontinued and the system was purged with nitrogen to remove the last traces of oxygen. Hydrogen, 7.1 SCFH, and methane, 21.32 SCFH, were flow-controlled to the dehydrogenator. The three-to-one methane to hydrogen approximates the composition of effluent gas from the hydrogenator. The system was placed under 10 psig pressure and the feed of the liquid condensate from the hydrogenator was commenced. The effluent from the dehydrogenator was condensed in equipment which was described above for the hydrogenation studies. The operating conditions and analyses of the product streams are summarized in Table V.

In both Tables IV and V, the temperature points or stations were identified as P-4 through P-18. The points are 12 inches apart, with P-5 being 4 inches below the top of each catalyst bed.

TABLE IV

HYDROGENATION OF PHENON

| Phenol(a) | | Gas Feed | | | Reactor | Gas | Ratio |
| Feed mls/hr | LHSV | Hydrogen ft³/hr | Methane ft³/hr | Space Velocity | Pressure psig | Blowoff ft³/hr | Hydrogen /phenol |
| --- | --- | --- | --- | --- | --- | --- | --- |
| 430 | 0.232 | 20.42 | 25.0 | 372 | 15.5 | 30.8 | 4.90 |
| 455 | 0.246 | 20.42 | 25.0 | 377.6 | 15.0 | 31.7 | 4.60 |
| 480 | 0.259 | 30.7 | 30.6 | 498 | 15.1 | 39.8 | 6.6 |
| 510 | 0.276 | 24.65 | 27.95 | 438 | 15.0 | 38.3 | 4.99 |
| 440 | 0.238 | 27.1 | 30.6 | 469.5 | 15.0 | 38.0 | 6.36 |
| 555 | 0.300 | 27.1 | 30.6 | 478.0 | 15.0 | 39.2 | 5.04 |
| 600 | 0.324 | 27.1 | 30.6 | 481.3 | 15.0 | 38.3 | 4.66 |
| 565 | 0.305 | 27.1 | 30.6 | 478.7 | 15.1 | 40.1 | 4.95 |

| Temperature, ° C. | | | | | | | |
| Pre-Heater p-4 | p-5 | p-6 | p-7 | p-8 | p-9 | p-10 | p-11–17 |
| --- | --- | --- | --- | --- | --- | --- | --- |
| 133 | 172 | 173 | 152 | 144 | 141 | 139 | 137–139 |
| 129 | 164 | 167 | 148 | 139 | 134 | 132 | 131–132 |
| 134 | 162 | 168 | 157 | 149 | 144 | 140 | 138–140 |
| 132 | 163 | 170 | 156 | 148 | 143 | 140 | 138–140 |
| 134 | 163 | 168 | 155 | 147 | 142 | 140 | 138–140 |
| 133 | 159 | 167 | 162 | 154 | 147 | 141 | 138–140 |
| 133 | 157 | 167 | 162 | 155 | 148 | 142 | 138–140 |
| 133 | 156 | 166 | 162 | 154 | 147 | 142 | 138–140 |

| Run Number | Cyclohexane | Benzene | Analysis (GC - Area %) | | | | Cyclohexanol/Cyclohexanone/Yield based on Phenol |
| | | | Cyclohexanone | Cyclohexanol | Dicyclohexyl ether | Phenol | |
| --- | --- | --- | --- | --- | --- | --- | --- |
| 1 | 0.21 | 0.53 | 3.56 | 94.45 | 1.20 | Trace | 98.01 |
| 2 | 0.16 | 0.46 | 2.17 | 96.29 | 0.89 | — | 98.46 |
| 3 | 0.16 | 0.32 | 2.52 | 95.88 | 1.10 | — | 98.4 |
| 4 | 0.19 | 0.57 | 3.0 | 95.3 | 0.94 | — | 98.30 |
| 5 | 0.20 | 0.55 | 2.74 | 95.6 | 0.88 | — | 98.34 |
| 6 | 0.21 | 0.73 | 3.44 | 94.9 | 0.74 | — | 98.34 |
| 7 | 0.13 | 0.50 | 3.12 | 95.4 | 0.88 | — | 98.52 |
| 8 | 0.13 | 0.47 | 3.04 | 95.4 | 0.94 | — | 98.44 |

(a) Contains 1.6 per cent water

TABLE V

DEHYDROGENATION

| | Cyclohexanol/ Cyclohexanone(a) | Gas Feed | | | Reactor | Gas |
| Run | Feed | Hydrogen | Methane | Space | Pressure | Blowoff |
| --- | --- | --- | --- | --- | --- | --- |

TABLE V-continued

| | | | DEHYDROGENATION | | | | |
|---|---|---|---|---|---|---|---|
| Number | mls/hr | LHSV | ft³/hr | ft³/hr | Velocity | psig | ft³/hr |
| 1 | 655 | 0.354 | 7.1 | 21.32 | 352 | 10 | 30.0 |
| 2 | 693 | 0.374 | 7.1 | 21.32 | 355 | 10 | 30.0 |
| 3 | 795 | 0.430 | 8.33 | 25.62 | 421 | 10 | 35.0 |
| 4 | 830 | 0.449 | 8.38 | 25.62 | 424 | 10 | 35.40 |
| 5 | 760 | 0.411 | 8.38 | 25.62 | 418 | 10 | 34.3 |
| 6 | 895 | 0.484 | 9.55 | 29.18 | 479 | 10 | 37.7 |
| 7 | 910 | 0.492 | 9.55 | 29.18 | 481 | 10 | 38.2 |
| 8(b) | 795 | 0.429 | 8.38 | 25.62 | 421 | 10 | 34.0 |

| | | | | Temperature, °C | | | |
|---|---|---|---|---|---|---|---|
| Pre-Heater p-4 | p-5 | p-6 | p-7 | p-8 | p-9 | p-10 | p-11–p-16(c) |
| 272 | 346 | 342 | 347 | 347 | 347 | 348 | 344–351 |
| 269 | 343 | 338 | 344 | 344 | 344 | 345 | 345–348 |
| 229 | 335 | 330 | 339 | 339 | 341 | 343 | 345–352 |
| 247 | 351 | 347 | 352 | 352 | 353 | 353 | 354–357 |
| 243 | 349 | 344 | 350 | 350 | 350 | 351 | 352–355 |
| 234 | 348 | 343 | 349 | 349 | 349 | 350 | 351–355 |
| 228 | 343 | 337 | 345 | 345 | 346 | 347 | 348–353 |
| 226 | 340 | 324 | 340 | 340 | 341 | 342 | 343–346 |

| | | | Analysis - Area % | | | | Cyclohexanol/Cyclo- |
|---|---|---|---|---|---|---|---|
| Run Number | Cyclo-hexane | Benzene | Cyclo-hexanone | Cyclo-hexanol | Dicyclo-hexyl ether | Phenol | Heavies | hexanone/Yield based on Phenol |
| 1 | 0.31 | 0.36 | 67.27 | 28.55 | 1.16 | 0.041 | 2.12 | 95.82 |
| 2 | 0.27 | 0.33 | 70.51 | 24.95 | 1.10 | 0.045 | 2.49 | 95.46 |
| 3 | 0.2 | 0.34 | 73.32 | 22.21 | 1.10 | 0.031 | 2.60 | 95.53 |
| 4 | 0.09 | 0.35 | 76.99 | 16.97 | 1.19 | 0.255 | 4.08 | 93.87 |
| 5 | 0.08 | 0.34 | 74.33 | 19.69 | 1.12 | 0.017 | 4.25 | 94.02 |
| 6 | 0.06 | 0.32 | 72.49 | 22.06 | 1.14 | Trace | 3.69 | 94.55 |
| 7 | 0.05 | 0.34 | 68.26 | 28.21 | 1.09 | Trace | 1.87 | 96.46 |
| 8 | 0.05 | 0.30 | 49.06 | 47.3 | 0.801 | 2.21 | 0.175 | 96.36 |

(a)Product from Hydrogenation of Phenol - 95% OL and 3% ONE
(b)Special feed OL = 88.5%, ONE = 7.64%, Phenol = 2.56%
(c)Catalyst bed ran to P-18 - Temperature at P-18 often dropped 10–20° C.

EXAMPLE 4

The laboratory scale hydrogenator was run in an additional series of experiments in which the ratio of hydrogen to phenol was varied. The conditions and results are shown below in Table VI:

the feed stream of the hydrogenator enables the hydrogenation to be carried out at efficiencies in excess of 99 per cent. Further, the use of diluted hydrogen enables an increase in the proportion of cyclohexanone product in the hydrogenation reaction. The data in Table VI illustrates how high a proportion of cyclohexanone can

TABLE VI

HYDROGENATION OF PHENOL

| Run Number | LHSV | Mols H₂: Mols Phenol | Space Velocity | Jacket °C | Catalyst Bed Inches from Top, °C | | | | | | |
|---|---|---|---|---|---|---|---|---|---|---|---|
| | | | | | 1 | 3 | 6.5 | 9.5 | 13 | 16.5 | 20 |
| 1 | 0.235 | 5:1 | 376 | 130 | 164.8 | 159.5 | 143.2 | 138 | 129.5 | 127.5 | 127 |
| 2 | 0.227 | 4:1 | 307 | 130 | 162.8 | 155 | 139.0 | 135.4 | 129.7 | 127 | 127 |
| 3 | 0.227 | 3.5:1 | 273 | 130 | 161.0 | 152.6 | 134.2 | 133 | 132.3 | 127.7 | 127.1 |
| 4 | 0.227 | 3:1 | 239 | 130 | 158.3 | 146.1 | 133.5 | 132.0 | 129.8 | 130.8 | 128.8 |
| 5 | 0.227 | 2.5:1 | 205 | 130 | 152 | 142 | 132 | 132 | 129 | 129 | 129 |
| 6 | 0.233 | 2.5:1 | 206 | 140 | 166.5 | 152 | 141.5 | 140 | 137 | 137 | 137 |
| 7 | 0.227 | 2.5:1 | 205 | 150 | 185.8 | 177.1 | 154.5 | 150.5 | 148.1 | 147.6 | 147.5 |
| 8 | 0.223 | 22:1 | 170 | 150 | 175.0 | 160.6 | 148.3 | 146.9 | 148.4 | 148.0 | 147.7 |

| | | | | | Gas Chromatographic Analyses, Area Percent | | | | | |
|---|---|---|---|---|---|---|---|---|---|---|
| Run Number | LHSV | Mols H₂: Mols Phenol | Space Velocity | Jacket °C | -One | -OL | Ether | Phenol | -OL/-One Ratio | -One + -OL |
| 1 | 0.235 | 5:1 | 376 | 130 | & 1.63 | 97.39 | 0.32 | 0 | 59.6 | 99.02 |
| 2 | 0.227 | 4:1 | 307 | 130 | 2.32 | 96.83 | 0.22 | 0 | 41.7 | 99.15 |
| 3 | 0.227 | 3.5:1 | 273 | 130 | 2.46 | 96.87 | 0.14 | 0 | 39.4 | 99.33 |
| 4 | 0.227 | 3:1 | 239 | 130 | 5.87 | 93.31 | 0.12 | & 0.24 | 15.9 | 99.18 |
| 5 | 0.227 | 2.5:1 | 205 | 130 | 13.74 | 74.94 | 0.12 | 10.89 | 5.45 | 88.68 |
| 6 | 0.233 | 2.5:1 | 206 | 140 | 20.17 | 79.03 | 0.13 | 0.14 | 3.92 | 99.20 |
| 7 | 0.227 | 2.5:1 | 205 | 150 | 28.99 | 69.17 | 0.13 | 1.19 | 2.39 | 98.16 |
| 8 | 0.223 | 22:1 | 170 | 150 | 38.08 | 49.91 | 0.02 | 11.70 | 1.31 | 87.99 |

Catalyst - Girdler G-87 300 ml (277 gms)
Phenol (U.S.P. grade) contains 1.61% Water
Reactor at 14 psig
-One = Cyclohexanone; Ether = Cyclohexylether
-OL = Cyclohexanol The Examples illustrate the advantages that can be obtained by practicing the invention. As the data in Table I show, the addition of small amounts of water to be produced, while still converting most of the phenol. In this respect, see Runs Nos. 6 and 7 in Table VI.

While the invention has been described in terms of using phenol as the reactant, alkylphenols, especially cresols, can also be used.

What is claimed is:

1. A vapor phase process which comprises contacting, in a catalyst zone, (a) phenol, and (b) a gas containing from about 30 to about 65 mole per cent hydrogen, the remainder of said gas being composed principally of at least one inert gas, with a metallic nickel hydrogenation catalyst, at an elevated temperature sufficient to produce cyclohexanol or a mixture of cyclohexanol and cyclohexanone, said elevated temperature being such that the temperature in said catalyst zone is within the range of from about 100° to about 230° C., and wherein said process is carried out at a pressure of up to about 3 atmospheres.

2. The process of claim 1 wherein said inert gas is methane.

3. The process of claim 1 wherein said phenol contains from about 0.5 to about 3 weight per cent water, based on weight of phenol.

4. The process of claim 3 wherein the inert gas is methane.

5. The process of claim 4 wherein the gas contains from about 45 to about 55 mole per cent hydrogen.

6. The process of claim 5 wherein said elevated temperature is within the range of from about 160° to about 180° C.

7. The process of claim 1 wherein the temperature in the catalyst zone is within the range of from about 160° to about 190° C.

8. The process of claim 1 wherein the molar ratio of hydrogen to phenol is within the range of from about 2:5:1 to about 6:6:1.

* * * * *

UNITED STATES PATENT OFFICE
CERTIFICATE OF CORRECTION

Patent No. 3,998,884      Dated December 21, 1976

Inventor(s) Charles Arnold Gibson

It is certified that error appears in the above-identified patent and that said Letters Patent are hereby corrected as shown below:

Column 3, line 1, after "160°C." insert -- to about 190°C. --

Column 8, TABLE I-continued, column of TABLE headed OL to ONE Ratio, Run No. 1, "&32.15" should read -- 32.15 --

Column 8, TABLE I-continued, column of TABLE headed "Phenol Conversion %", Run No. 19, "96.77" should read -- 99.77 --

Column 11-12, TABLE IV, Title "HYDROGENATION OF PHENON" should read -- HYDROGENATION OF PHENOL --

Column 13-14, TABLE VI-continuation, column of TABLE headed "-One", Run No. 1, "&1.63" should read -- 1.63 --

Column 13-14, TABLE VI-continuation, column of TABLE headed "Phenol", Run No. 4, "&0.24" should read -- 0.24 --

Signed and Sealed this twelfth Day of July 1977

[SEAL]

Attest:

RUTH C. MASON
*Attesting Officer*

C. MARSHALL DANN
*Commissioner of Patents and Trademarks*